(12) United States Patent
Steiger (10) Patent No.: US 11,793,665 B1
(45) Date of Patent: Oct. 24, 2023

(54) VENTED DENTAL APPLIANCE FOR BRUXISM RELIEF

(71) Applicant: Gregory Todd Steiger, San Anselmo, CA (US)

(72) Inventor: Gregory Todd Steiger, San Anselmo, CA (US)

(*) Notice: Subject to any disclaimer, the term of this patent is extended or adjusted under 35 U.S.C. 154(b) by 0 days.

(21) Appl. No.: 17/721,130

(22) Filed: Apr. 14, 2022

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ...... A61F 5/56; A61F 5/566; A61F 2005/563; A61C 7/08; A61C 7/36; A63B 71/085; A63B 2071/086; A63B 2071/088
See application file for complete search history.

(56) References Cited

U.S. PATENT DOCUMENTS

| | | | |
|---|---|---|---|
| 5,921,240 A | 7/1999 | Gall | |
| 5,950,624 A | 9/1999 | Hart | |
| 6,755,191 B2 * | 6/2004 | Bertoch | A61M 16/0493 128/207.14 |
| 8,316,859 B2 | 11/2012 | Lesniak | |
| 8,464,709 B2 | 6/2013 | Wedemeyer | |
| 10,080,680 B2 | 9/2018 | Magness | |
| D871,571 S | 12/2019 | Chen | |
| 10,898,369 B2 | 1/2021 | Farrell | |
| 10,945,874 B2 | 3/2021 | Akervall et al. | |
| 11,000,404 B2 | 5/2021 | Hamburg | |
| 11,007,076 B1 | 5/2021 | Hamrah et al. | |
| 11,033,421 B1 | 6/2021 | Davis | |
| 11,058,571 B2 | 7/2021 | Brown | |
| 11,129,746 B2 | 8/2021 | Alvarez et al. | |
| 11,123,219 B2 | 9/2021 | Tamez | |
| 2017/0151400 A1 * | 6/2017 | Vaska | A61M 16/0488 |

* cited by examiner

Primary Examiner — Camtu T Nguyen
(74) Attorney, Agent, or Firm — Boris Leschinsky (57) ABSTRACT

A vented dental appliance for relief of bruxism includes an intraoral retainer such as a flexible plate positioned between the teeth and the cheeks of the user. An elongated vent member is slidably positioned through one of a plurality of apertures in the intraoral retainer and includes at least a first fluid conduit connecting the intraoral space and the extraoral space. The intraoral portion of the vent member features multiple intraoral vent openings positioned along thereof and configured to prevent internal blockage by a tongue or other soft tissue inside the mouth. The extraoral portion is open and configured to vent the intraoral space to atmosphere, thereby relieving the intraoral suction and allowing for jaw muscles to relax. In other embodiments, the intraoral retainer may be a dental guard or another more advance dental appliance.

18 Claims, 7 Drawing Sheets

VENTED DENTAL APPLIANCE FOR BRUXISM RELIEF

BACKGROUND

Without limiting the scope of the invention, its background is described in connection with dental appliances. More particularly, the invention describes a vented dental appliance for the relief of symptoms associated with bruxism.

Bruxism is a condition associated with excessive teeth grinding and/or clenching of a jaw. It is a common behavior among both children and adults. For example, in the US alone, this condition is clinically diagnosed over 200,000 times a year. Some estimates point to a broad prevalence of this condition in the general population, which ranges from 8 to as much as 31 percent. There are two main types of bruxism: one occurs during sleep (nocturnal bruxism) and one during wakefulness (awake bruxism). Dental damage may be similar in both types, but the symptoms of sleep bruxism tend to be worse on waking and improve during the course of the day, and the symptoms of awake bruxism may not be present at all on waking, and then worsen over the day. While some people don't have any symptoms, others may experience headaches, jaw pain, tooth pain, or develop other dental problems. In some cases, it can cause irreversible damage to teeth and the temporomandibular joint (TMJ). For example, bruxism may contribute to a temporomandibular disorder (TMD).

Various night guards and other dental appliances are routinely used for treating the symptoms of nocturnal bruxism—some with better success than others. Yet, many patients still report unsatisfaction and continuation of their symptoms despite using these devices. The need exists therefore for a better dental appliance to relieve symptoms of bruxism, and in particular, nocturnal bruxism, which exhibits higher efficacy for a broader range of patients.

One particular problem that is not addressed by dental appliances of the prior art is the presence of persistent suction or vacuum (these terms are used interchangeably in this description) in the enclosed space above the tongue when the mouth is closed. Whether intentionally or unintentionally, many people develop this suction when their jaws are clenched, and their jaw and other oral muscles are in tension. This phenomenon is exacerbated during sleep when a person is not able to consciously relax the muscles and vent the suction. Once the suction is created, relaxing the muscles may be difficult as it acts to persistently pull all soft tissue together in a tight space—regardless of whether there is a conventional dental appliance present or not. The need, therefore, exists for an improved dental appliance capable of relieving the suction in the mouth and facilitating bruxism relief.

SUMMARY

Accordingly, it is an object of the present invention to overcome these and other drawbacks of the prior art by providing a novel vented dental appliance designed to relieve intraoral suction and facilitate relaxation of various jaw and mouth muscles.

It is another object of the present invention to provide a novel vented dental appliance capable of adjusting of positions of various components thereof so as to improve comfort for the user.

It is a further object of the present invention to provide a vented dental appliance configured to reduce or eliminate inadvertent saliva leaks from the mouth during sleep.

The vented dental appliance of the invention includes an elongated vent member comprising at least a first fluid conduit. The first fluid conduit in turn includes an intraoral portion and an extraoral portion. The intraoral portion features multiple intraoral vent openings positioned along thereof and configured to prevent internal blockage by a tongue or other soft tissue inside the mouth. The extraoral portion has at least one or more extraoral openings so as to vent the first conduit to atmosphere.

The elongated vent member may be retained inside the mouth of the user by an intraoral retainer. In its most basic form, the intraoral retainer is a flexible plate positioned between the teeth and the cheeks of the user. In other embodiments, the intraoral retainer may be a dental guard or another more complicated dental appliance.

Since the use of the vented dental appliance is expected to occur in users with different size and shape of their mouths and with significant differences between the location and shape of various teeth inside the mouth, it is important to provide the dental appliance with an ability to be adjusted so as to improve the comfort of the user. As the elongated vent member is designed to cross over from the inside of the mouth to the outside of the mouth, it has to cross a pair of adjacent upper and lower teeth in at least one location. To facilitate adjustment of that location, the intraoral retainer is designed to allow the elongated member to slide in and out of an aperture across thereof providing for some flexibility in selecting a position of the elongated vent member inside the mouth.

In addition, one or more alternative apertures in the intraoral retainer may be provided to allow sliding of the elongated vent member out of one aperture and insertion into an adjacent aperture. Once inserted into an aperture of the intraoral retainer, the elongated vent member is retained therein, for example by friction or by a retaining grommet, so as to fix its position. Yet, when pulled using a force exceeding a predetermined pull threshold, the elongated vent member may still be repositioned further until the most comfortable location is identified.

Apertures may be made by creating a suitable opening in the intraoral retainer. In alternative designs, the location of some or all apertures may be accompanied by reinforcement embedded in the wall of the intraoral retainer, such as a locally increased wall thickness or an embedded reinforcement ring. Aperture reinforcement may be instrumental in reducing aperture elongation or another deformation during use and preventing inadvertent damage such as rupture of the wall of the retainer between adjacent apertures.

Changing the position of the elongated vent member within the intraoral retainer may also have a clinically beneficial effect in addition to improving comfort. Reconfiguring the appliance or intermittently stopping its use altogether may provide the additional benefit of not acclimating to the initial configuration, which otherwise may cause a return of jaw clenching symptoms.

In use, the elongated vent member provides for continuous fluid communication between the inside of the mouth (intraoral space) and atmosphere (extraoral space), thereby relieving any possible suction that may be developed by the user, for example, while clenching the jaws or as a result of other actions.

An anti-drooling slideable soft grommet may also be provided to reduce the risk of inadvertent saliva leak from the mouth while the vented dental appliance of the invention is in use. The anti-drooling grommet may have an elongated cross-section so as to follow the expected contour of the lips when the mouth is closed and the appliance is in use. Further anti-drooling protection may be provided by using one or more check valves positioned at the intraoral ends of one or more conduits. These check valves may be configured as simple flaps configured to allow air from outside to come into the intraoral cavity but prevent saliva from leaking outwards.

In addition to relieving symptoms of bruxism, the vented dental appliance of the present invention may be useful to relieve other similar conditions, for example, morsicatio buccarum (chronic cheek chewing/biting) and others.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

FIGS. 1 through 5 show various views of the first embodiment of the present invention. The vented dental appliance 10 broadly comprises an intraoral retainer 12 configured to position the elongated vent member 20 inside the intraoral cavity of the user such that at least an extraoral portion of the vent member provides for relief of an intraoral suction via venting the intraoral cavity to atmosphere.

Approximate dimensions of the dental appliance may be from about 5 cm to 7 cm wide, about 4 cm to 6 cm long, about 12 mm to 30 mm high, and about 1 mm to 20 mm deep. The peripheral length of the intraoral retainer may be about 10 cm to 12 cm long. The dental appliance may be configured to be oriented and aligned with the upper teeth, with the lower teeth, or both. The dental appliance may also be configured to allow the user to flip the appliance such that its upper portion becomes its lower portion. This may be beneficial to change the contact points between the appliance and the mouth tissues so as to avoid getting used to the dental appliance, which may precipitate a return of the bruxism symptoms.

Figure 1:
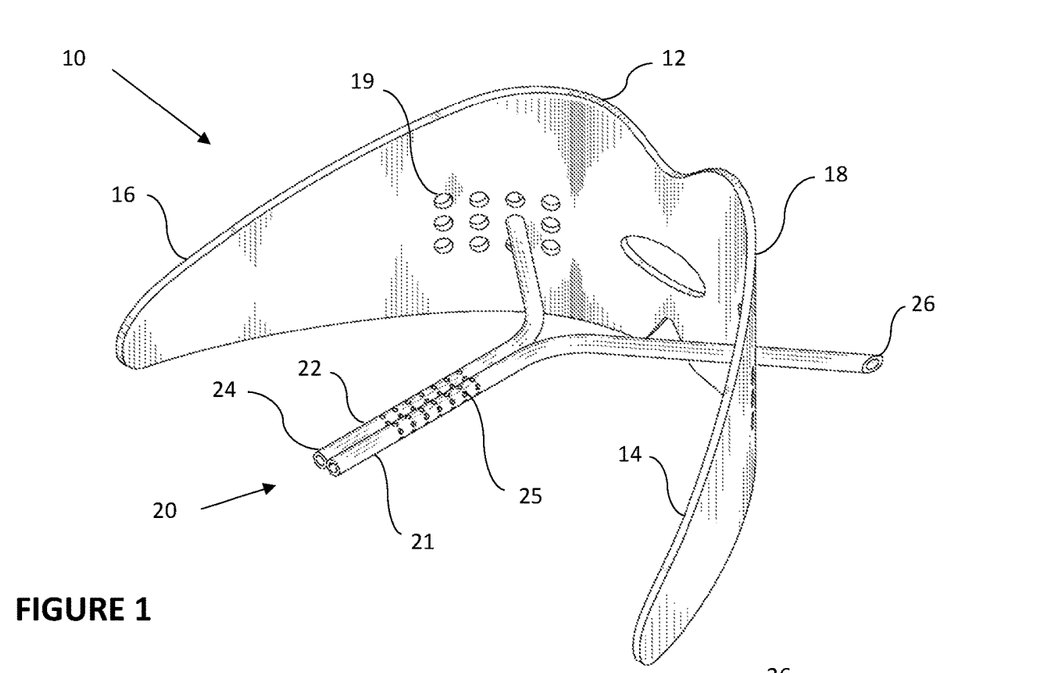
FIG. 1 is a perspective view of the first embodiment of the invention.
Figure 2:
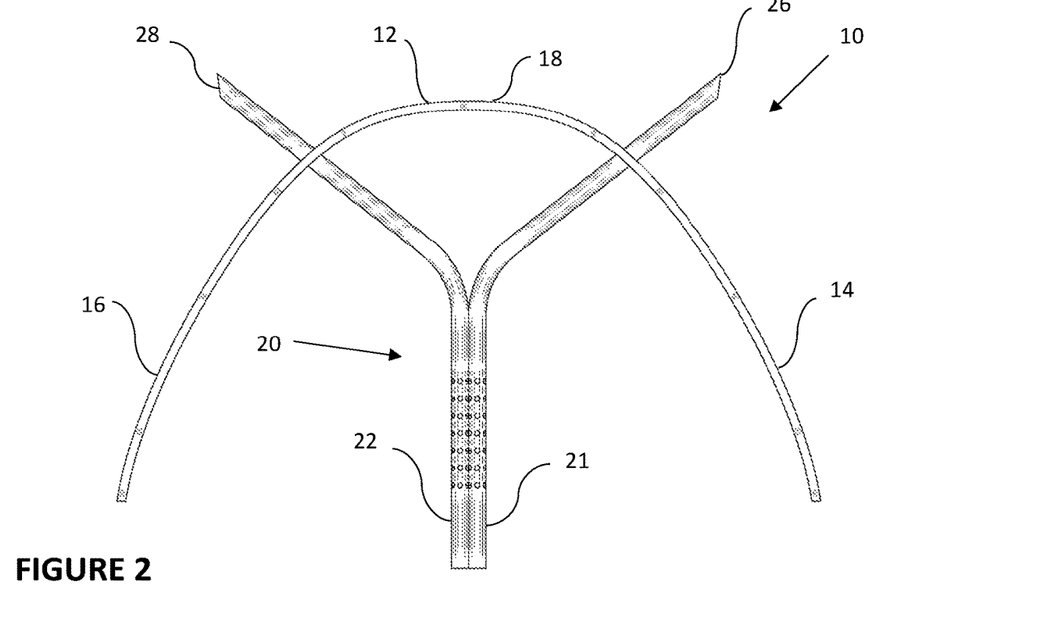
FIG. 2 is a top view of the same.

The intraoral retainer 12 of this embodiment may include a flexible plate 18 made in a shape suitable to be placed between the teeth and the cheeks of the user. It may be made from a flexible biocompatible material, such as polyurethane, silicone, or another suitable plastic film with a thickness of about 0.1 to 3 mm—made as a clear or a colored structure. It may have a predetermined contour or may include an ability to be trimmed by the user as the invention is not limited in this regard. The intraoral retainer 12 may be further configured for ease of washing or rinsing between uses so as to maintain its surfaces in a clean state.

The intraoral retainer 12 may further include two sides: a right side 14 and a left side 16. Both sides 14 and 16 may be similarly contoured and may be symmetrical about the central vertical line (not shown) located in the middle of the intraoral retainer 12. Each side may extend towards approximately a location of the farthest back molars, such as approximately to the $3^{rd}$ molar location in adults and $2^{nd}$ molars in children. A suitably shaped top and bottom indentations or notch-shaped cut-outs may be provided to avoid compressing intraoral structures when the dental appliance is in use. Other suitably shaped contours of the intraoral retainer 12 may also be used as the invention is not limited in this regard.

Figure 6:
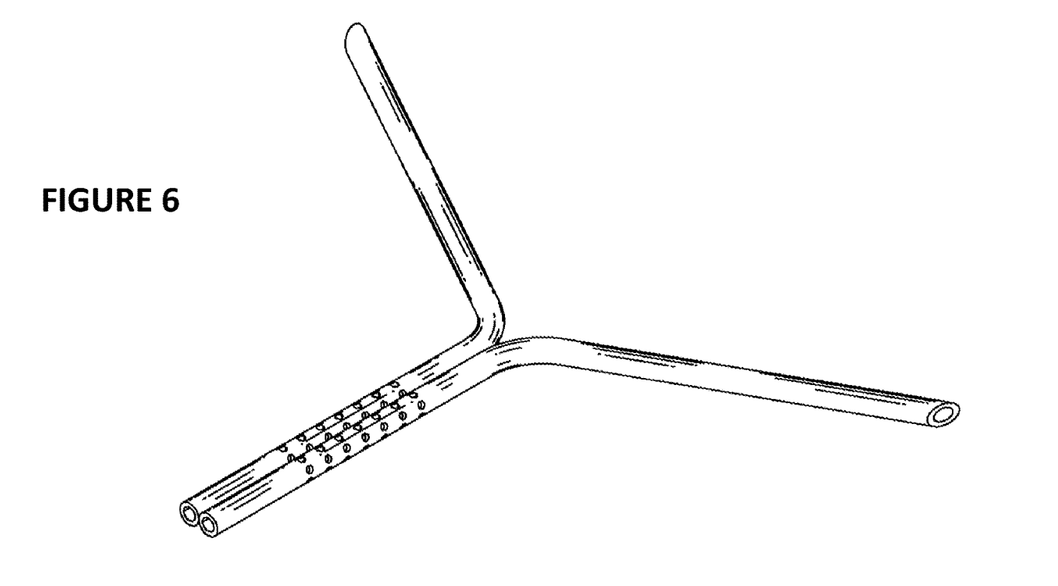
FIG. 6 is a perspective view of the elongated vent member.
Figure 7:
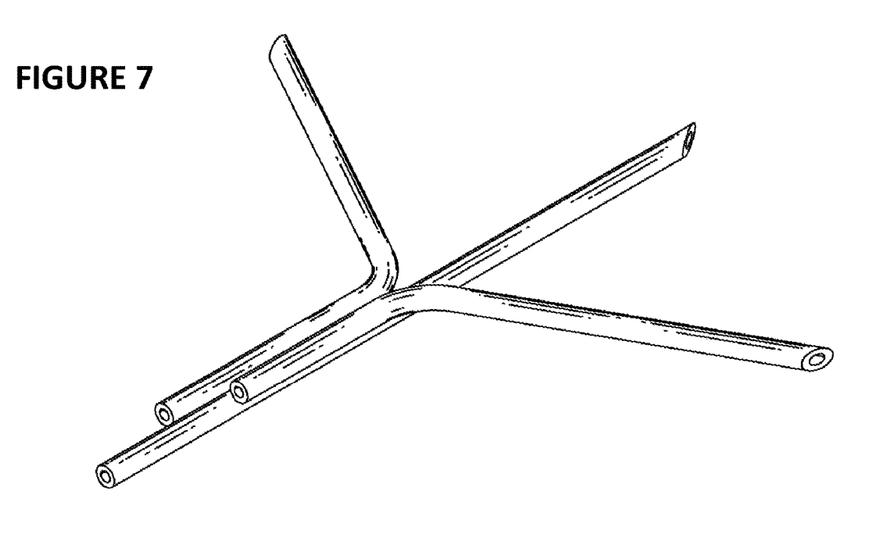
FIG. 7 is a perspective view of an alternative design for the elongated vent member.
Figure 8:
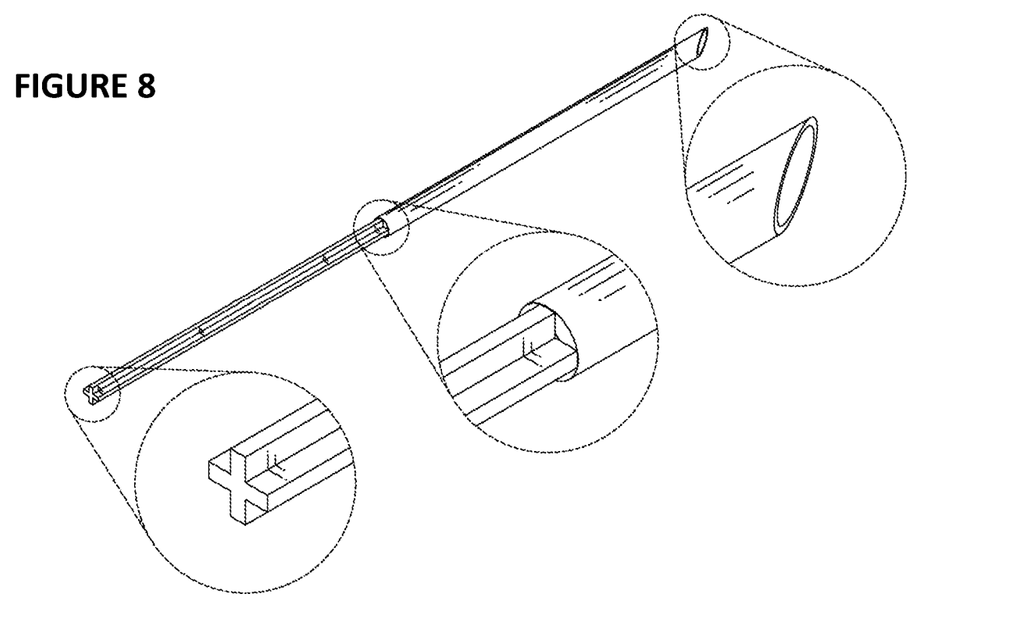
FIG. 8 is a close-up of yet another design of the elongated vent member.

The elongated vent member 20 is seen in FIGS. 1-5 as assembled with the intraoral retainer 12 and its various designs are shown separately in FIGS. 6-8. It may include at least a first conduit 21, or in other alternative designs, a second conduit 22, as well as a third conduit or more conduits in further alternative designs. Each conduit may include at least a portion thereof with internal reinforcement, preferably at the expected location where the conduit crosses over the wall of the intraoral retainer so as to increase resistance to compression and prevent undesirable kinking or crushing during use.

Shown in FIGS. 1-5 is a design having a first conduit 21 and a second conduit 22. Each conduit may define an intraoral portion inside the boundaries of the intraoral retainer and an extraoral portion where the vent member protrudes outside the intraoral retainer to reach extraoral space outside the mouth of the user at respective openings 26 and 28. Openings 26 and 28 may be cut at an angle to prevent its blockage outside the mouth (for example, by a sleeping pillow) as well as to facilitate insertion of the conduits through apertures 19 during the process of adjustments to achieve the most comfortable configuration of the device. The two conduits 21 and 22 may be fused or otherwise joined together along at least some part of their respective intraoral portions, such as about 15 mm to 30 mm in length. Conduits 21 and 22 may bifurcate and extend across the intraoral retainer at an angle of about 30 to 150 degrees between them. In embodiments that lack occlusal elements, each conduit may be located in a gap in between adjacent teeth of the user. Each conduit may have one or more end openings 24 as well as one or more additional intraoral openings or perforations 25 so as to reduce the risk of inadvertent occlusion of the conduit by a tongue or other soft tissues inside the mouth. The diameter of the perforations 25 in the intraoral portion of the conduit may vary from about 0.25 mm to about 1.5 mm to allow adequate venting and ease of rinsing with water. With an average size of 0.75 mm, there would typically only need to be 6 or 7 perforations. Locations of these perforations may be spaced out longitudinally along the conduit tubing. In other contemplated embodiments, spacing between and positions of perforations may vary—such as being spaced apart in a radial or spiral manner (not shown in the drawings), with each successive perforation located at about 45-135 degrees off from the previous location.

In embodiments, each conduit may be made from flexible tubing made of a biocompatible polymer material. The length of each conduit may be about 30 to 80 mm and may be configured to be trimmable by the user. The intraoral portion length may be selected to assure that the conduits 21 and 22 protrude towards a location between the front portion of the tongue and the mouth roof when the tongue is relaxed. A shorter length may not be effective in relieving the suction while a longer length may cause an undesirable gagging reflex.

The inside diameter of each conduit may be from at least about 0.5 mm to about 3 mm, such as at least 0.5 mm, at least 1 mm, at least 1.5 mm, at least 2 mm, at least 2.5 mm, or about 3 mm as the diameter is selected to assure adequate venting but be as small as possible to improve comfort in use. The wall thickness may be selected to reduce the risk of kinking and provide adequate resistance to crushing force, but at the same time assure adequate flexibility and improve comfort. In embodiments, the wall thickness may be selected to be from about 0.25 mm to about 2 mm, such as at least 0.25 mm, at least 0.5 mm, at least 1 mm, at least 1.5 mm, or about 2 mm. Given these ranges of internal diameters and wall thicknesses, the outside diameter of the conduit may range from about 1 mm to about 5 mm.

Figure 3:
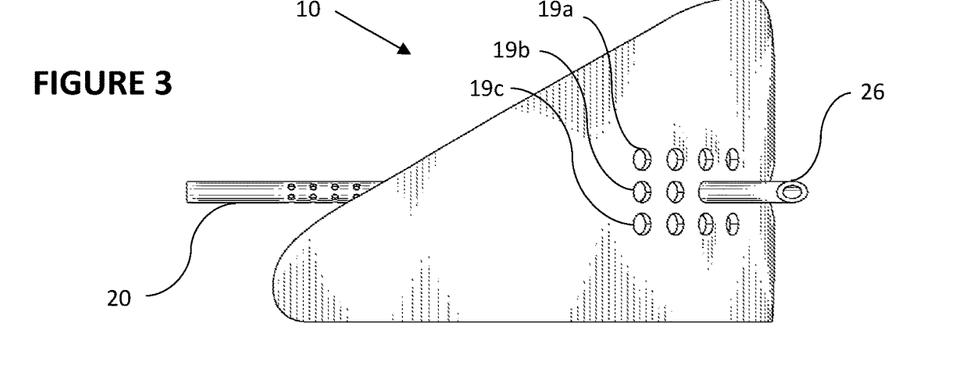
FIG. 3 is a side view of the same.
Figure 4:
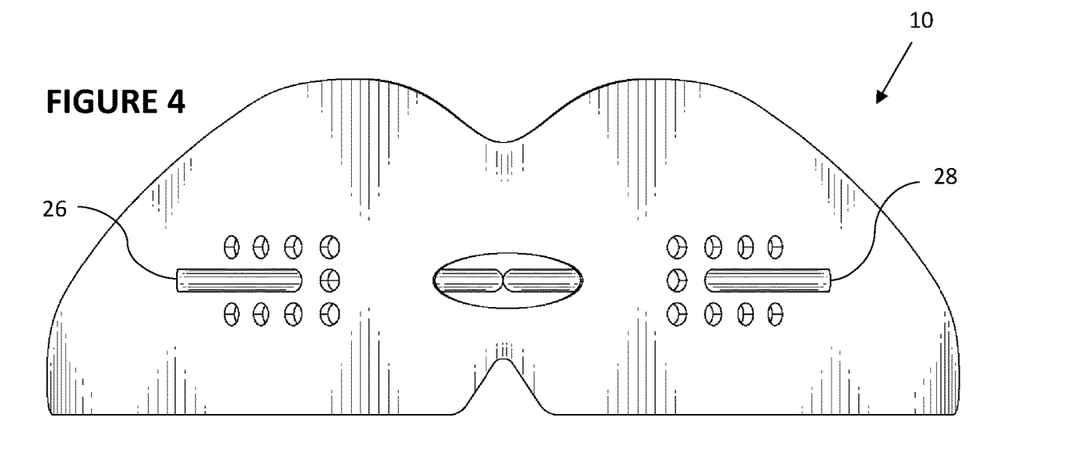
FIG. 4 is a front view of the same.
Figure 5:
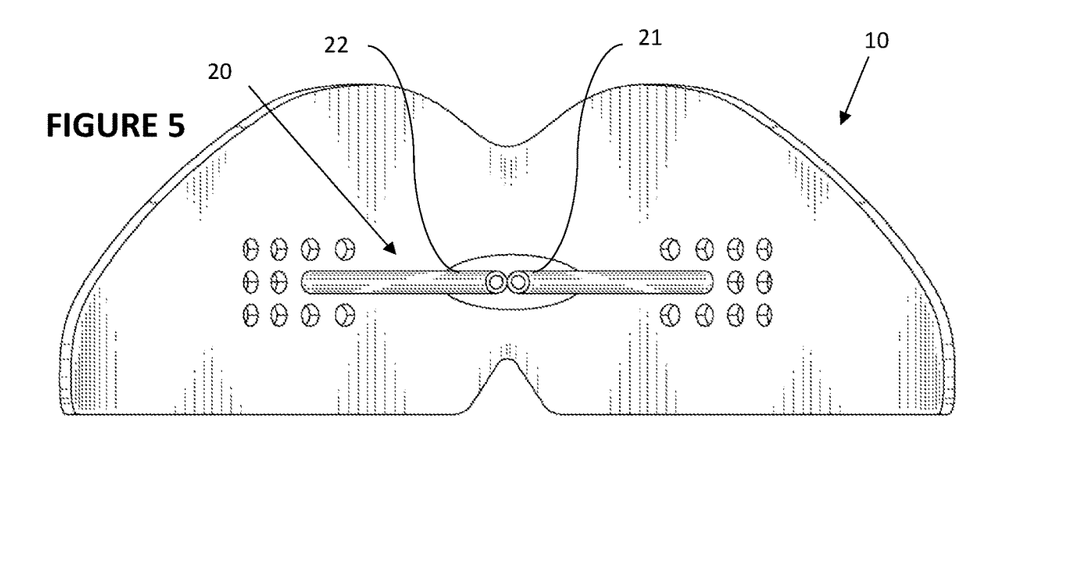
FIG. 5 is a back view of the same.

Each of the two conduits 21 and 22 is retained by the intraoral retainer 12 at one of a plurality of apertures 19 made at both sides 16 and 14 of the intraoral retainer. A plurality of apertures 19 may be arranged in multiple rows 19a, 19b, 19c as seen in FIG. 3 with each row having at least 1 or more apertures, such as at least 1 aperture, at least 2 apertures, at least 3 apertures, at least 4 apertures, at least 5 apertures or more as the invention is not limited in this regard. At least two rows of apertures may be arranged to be parallel to each other. The apertures may be spaced from each other by 1-6 mm. The spacing between the apertures may be uniform or not as the invention is not limited in this regard. In one contemplated embodiment, the spacing between the apertures may be made in a predetermined alternating ratio (not shown in the drawings), for example, 2:3:2:3:2:3 and so on.

Switching from one aperture to another allows the user to change the position of the conduit located across the intraoral retainer which is helpful in finding the most comfortable location therefor. As different users may have different locations of various anatomical features and teeth in the mouth. Because of that, switching the position of the conduit located across the intraoral retainer helps in finding the location where the conduit lies in between the biting surfaces of the adjacent upper and lower teeth which makes it less intrusive for the user.

Advantageously, the user can adjust the position of the conduit in horizontal (lateral) as well as vertical directions, thereby providing maximum flexibility for the user in selecting the best position for each conduit. Locations of the apertures are suitably made to cover a range of horizontal and vertical positions, as can be understood by those skilled in the art.

The size of each aperture 19 may be selected to retain the vent member therein with a certain minimum pull force. In other words, sliding the conduit in or out of the aperture may only be accomplished when the pull force exceeds a certain predetermined pull threshold. The purpose of this is to provide for stability of the conduit location during normal use but also to allow adjustments to be made if needed by repositioning the conduit in the same aperture 19 or switching to another aperture 19 altogether, both in horizontal as well as vertical directions.

In embodiments, the size of the aperture 19 may be selected to be the same as the outside diameter of the conduit 21 or 22. To increase the friction fit, the size of the aperture 19 may be selected to be smaller than the outside diameter of the conduit, such as about 70% to 99% thereof so as to provide some compression of the conduit tubing but without compromising its ability to vent the intraoral cavity to atmosphere. In various embodiments, the relative size of the apertures 19 may be selected to be at least 70%, at least 75%, at least 80%, at least 85%, at least 90%, at least 95%, or about up to 99% of the outside diameter of the respective conduit tubing.

Selecting the size of the aperture to be at or smaller than the size of the conduit leads to an increased pull force necessary to move the conduit in or out of the intraoral retainer. In embodiments, the minimum suitable pull threshold may be selected to be from about 0.25 lbs to 5 lbs, such as at least 0.25 lbs, at least 0.5 lbs, at least 0.75 lbs, at least 1 lb, at least 1.5 lbs, at least 2 lbs, at least 3 lbs, at least 4 lbs, or up to 5 lbs.

In addition to providing prefabricated apertures 19 as part of the intraoral retainer, the elongated vent member may be provided together with a suitable punch to make additional apertures at user-selected locations. Providing a corresponding aperture punch along with the elongated vent member as a stand-alone kit may also be useful for adapting a conventional or customized mouthguard for the inclusion of the elongated vent member of the invention and converting a conventional mouthguard for the purposes of venting the intraoral suction during sleep.

Using an aperture punch may permit providing the intraoral retainer with the desired number of apertures with or without any prefabricated apertures so that the user may make these apertures based on personal preferences. A template or a guide may be provided suggesting a suitable location for these apertures. Alternatively, suggested positions of the apertures may be marked on the intraoral retainer itself.

FIG. 6 shows the same design for the vent member as in FIG. 1 through FIG. 5. FIG. 7 shows an alternative design with three conduits and a staggered location of intraoral openings inside the mouth. In addition to collecting all conduits together in a triangular shape arrangement shown in the figures, these three or more conduits may be arranged to be located side by side in a flat "ribbon" manner (not shown in the drawings).

FIG. 8 shows a further yet alternative design of the elongated vent member. In this case, at least a part of its length is made from a multi-side extruded profile and not as a tube. The multi-side profile may have 3, 4 (as seen in the drawings), 5, 6, or more sides extending radially from the centerline of the conduit. Further yet designs may be contemplated for use as an alternative design for the vent member (not shown) as the invention is not limited in this regard. Examples of further designs may include a continuous spiral shape elongated to form a hollow tube, a serpentine arrangement of convoluted plastic patterns also forming an elongated tube shape, tubing made with an oval cross-section, etc. as long as continuous fluid communication is provided between the intraoral space and the extraoral space to relieve the intraoral suction.

Figure 9:
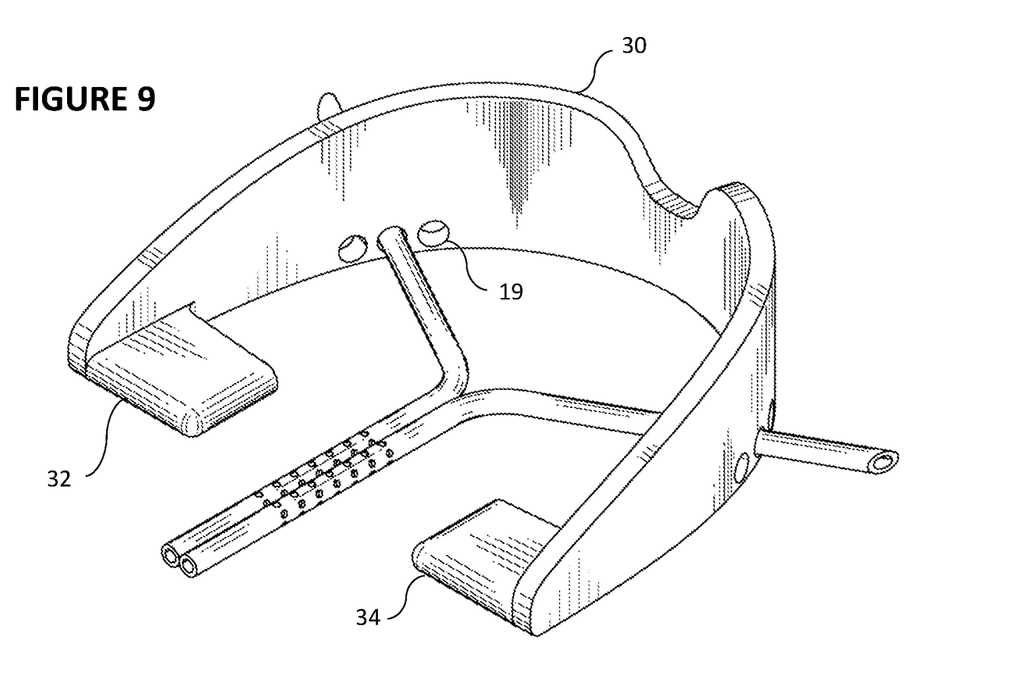
FIG. 9 is a perspective view of a second embodiment of the invention.

FIG. 9 shows a second embodiment of the invention, in which the intraoral retainer 30 contains two bite plates 32 and 34 on both ends thereof for better retention of the dental appliance inside the mouth as well as the presence of some minimal amount of physical occlusal material for those who may be more prone to strong clenching. A further change is the presence of only one row of apertures 19 at the bottom of the intraoral retainer 30.

Figure 10:
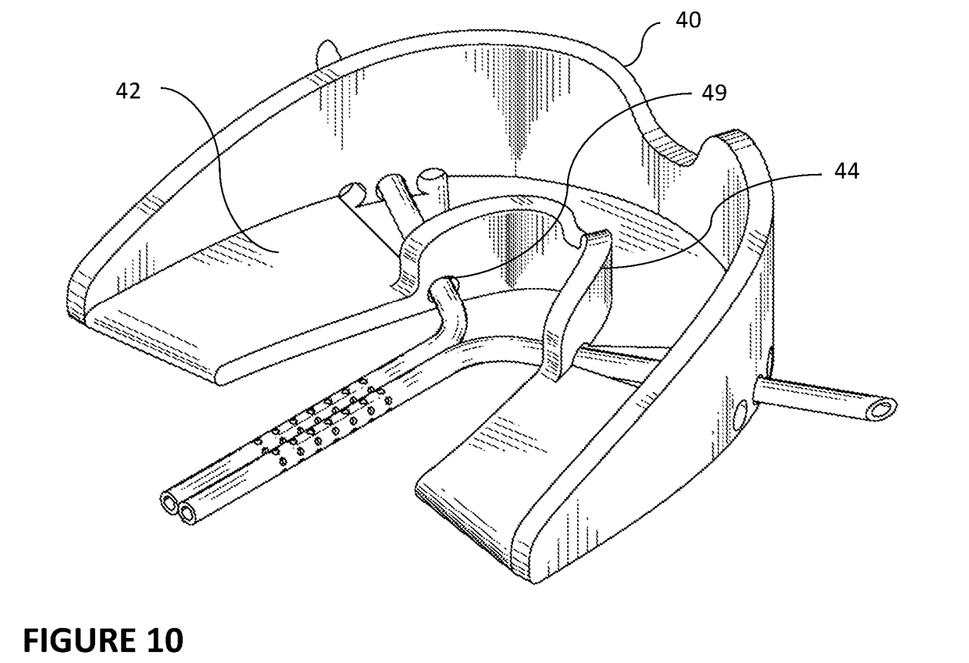
FIG. 10 is a perspective view of a third embodiment of the invention.

FIG. 10 shows a third embodiment of the vented dental appliance of the present invention in which the intraoral retainer 40 is further built-up with the full occlusal plate 42 extending along the full length thereof and a partial lingual plate 44 having additional apertures 49 for removable retention of the elongated vent member therein.

Figure 11:
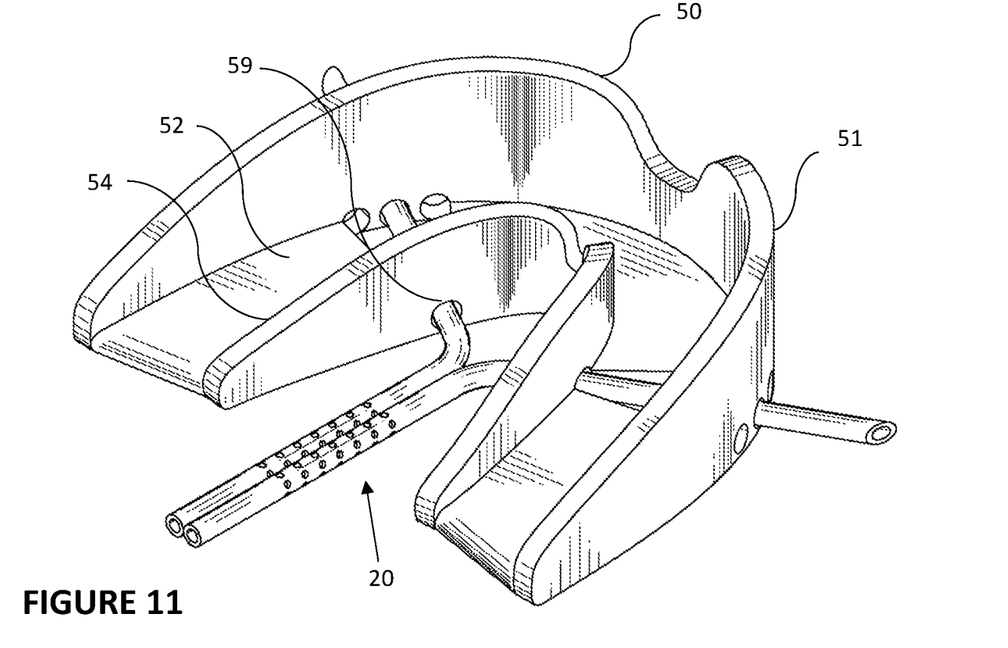
FIG. 11 is a perspective view of a fourth embodiment of the invention.

FIG. 11 shows a further yet fourth embodiment of the present invention in which the intraoral retainer 50 includes a full buccal plate 51, full occlusal plate 52, and full lingual plate 54 with additional apertures 59 in the lingual plate 54 for retaining the elongated vent member 20 therein.

Figure 12:
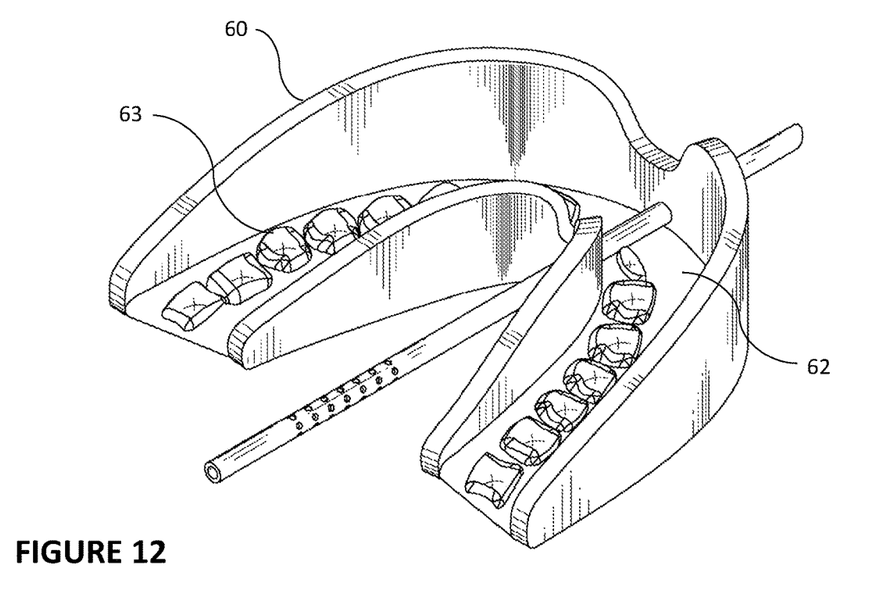
FIG. 12 is a perspective view of a fifth embodiment of the invention.

FIG. 12 shows a fifth embodiment of the invention in which the intraoral retainer 60 contains an occlusal plate 62 with impressions 63 corresponding to the respective teeth of the user. In this case, the intraoral retainer 60 is made as a full mouthguard with a custom shape for each user, thereby further improving the comfort when the device is in use. As known in the art, these custom mouth guards may be produced using a variety of known techniques, such as produced in the lab using custom impressions or intraoral scans, boil-and-bite technique, as well as other methods. The same manufacturing methods may be applicable to various embodiments of the present invention as well. In further embodiments, the wall of the intraoral retainer 60 may be shortened and extended past the occlusal plate only to a sufficient extent to house the apertures needed for retention of the elongated vent member in place.

Figure 13:
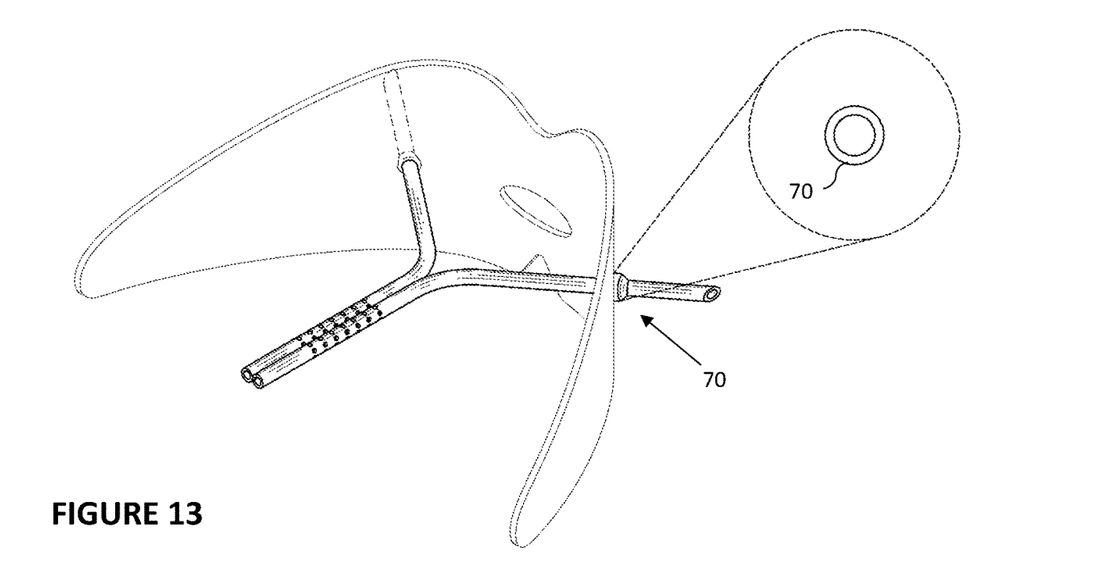
FIG. 13 is a perspective view of the elongated vent member retained at the intraoral retainer by the use of grommets.
Figure 14:
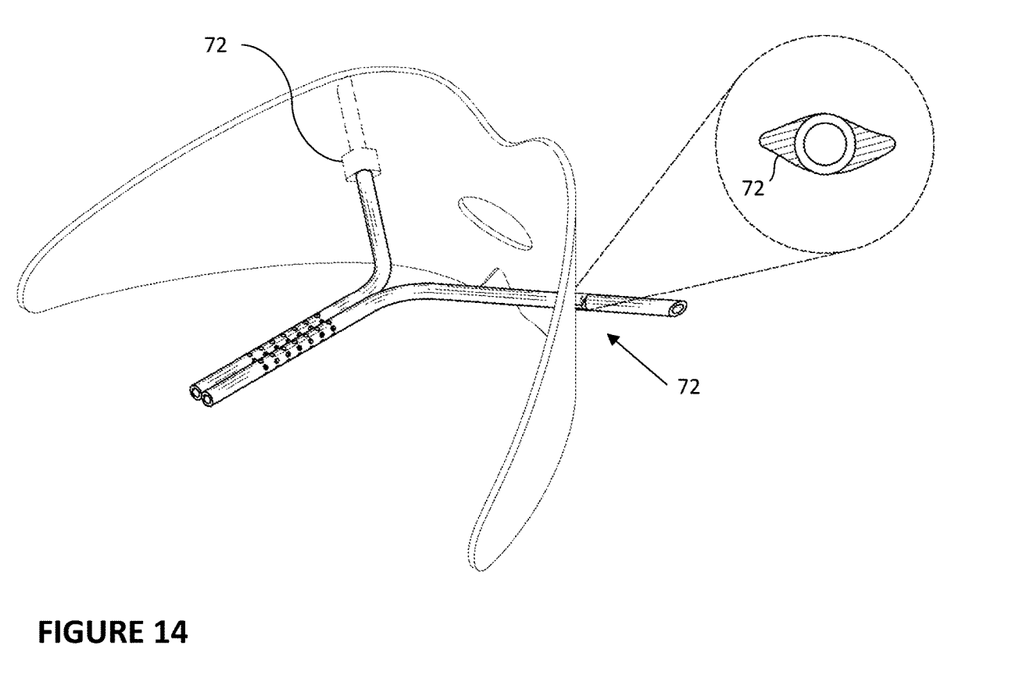
FIG. 14 shows an alternative design of the grommets.
Figure 15:
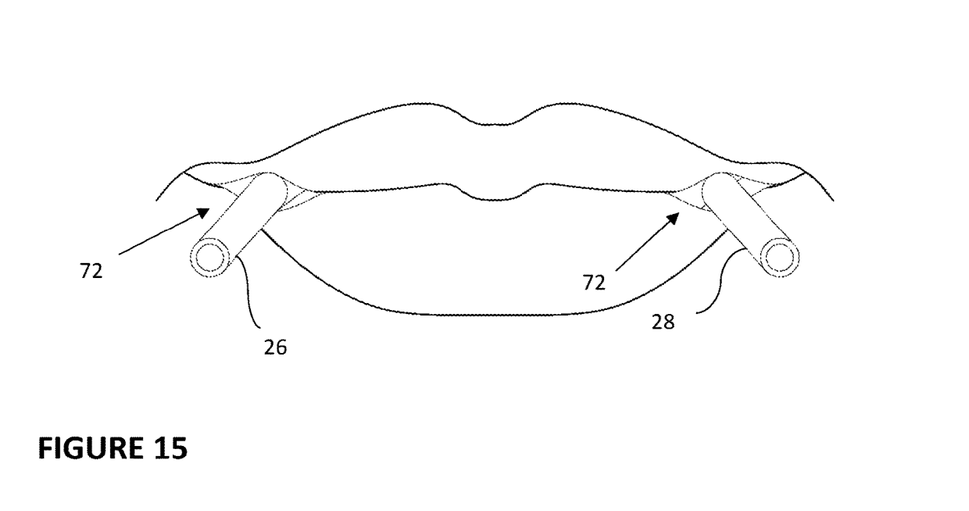
FIG. 15 shows the dental appliance with grommets of FIG. 14 in use.

FIGS. 13 through 15 show further embodiments of the vented dental appliance according to the present invention. Retention of the elongated vent member within the intraoral retainer is accomplished by using at least one grommet on each of the conduits of the elongated vent member. FIG. 13 shows the use of a single round grommet 70 assembled over the extraoral portion of the conduit. The conduit itself may be slidingly retained across a corresponding aperture in the intraoral retainer with minimum or no sliding friction. The presence of the grommet 70 over the conduit assures that it cannot be slidingly removed from the intraoral retainer without encountering the grommet 70 along the way. In some embodiments, the grommet 70 may be permanently attached to the conduit. In this case, pulling the conduit from the inside of the intraoral retainer would cause a temporary deformation of the grommet and a temporary enlargement of the aperture in the intraoral retainer so as to pass the grommet through that aperture.

The shape of the grommet 70 may have a taper or a leading edge on one or both ends thereof so as to aid in pulling the conduit from the aperture. FIG. 13 shows a taper on the external end of the grommet 70 which may be helpful in securing the conduit in the desired aperture when pulling the conduit and the grommet therethrough. Absence of the leading edge on the other side of the grommet may be useful to increase resistance against pulling the conduit in the other direction, thereby increasing the safety margin of the location of the conduit without the risk of undesirable dislodgement thereof.

In further embodiments, the grommet 70 may be made to slide over the respective conduit of the elongated vent member. In this case, the force needed to move the location of the grommet 70 along the conduit may be selected in a manner similar to that of the previous embodiments in which the position of the conduit was limited by a pull force across the aperture on the intraoral retainer itself. In various embodiments, the aperture size across the intraoral retainer may be selected to not impart a significant sliding resistance on the conduit as the function of limiting its position is shifted to the grommet located on the conduit.

The grommet material may be selected from a range of biocompatible polymers, such as polyurethanes, silicones, and other suitable polymers. Using the same material for making both the conduit and the overlaying grommet may be advantageous when fusing them together.

In a further design alternative, a pair of grommets may be used on each conduit, one located on one side of the intraoral retainer aperture and the other grommet located on the other side thereof. Shifting the position of one or both of the pair of grommets allows the user to adjust the position of the conduit across the intraoral retainer until the most comfortable location is found.

In further embodiments, positioning of one or more conduits across the lips of the user may cause undesirable leakage of saliva during sleep. This may be caused by the lips being unable to seal the space around the circular conduit. To address this problem, the grommet 72 (see FIGS. 14 and 15) may be provided having an elongated cross-sectional shape. In embodiments, a ratio between the length and the width of the grommet in its cross-section may vary from 1.1 to 8, such as at least 1.1, at least 1.2, at least 1.5, at least 1.7, at least 2, at least 3, at least 4, at least 5, at least 6, at least 7, or about 8. When an elongated grommet 72 is used, the longer side thereof may be turned to be located between the lips of the user so as to block the space on both sides of the circular conduit extending therefrom. The ends on both sides of the elongated cross-section may be sharp or rounded. The sharp ends may be advantageous for a complete seal of the space between the lips. It would not pose a safety problem as the grommet material is soft and flexible so no risk of cutting intraoral tissues is expected.

The entire device of any of the embodiments may be appropriately scaled to make a vented dental appliance in various sizes, such as at least one adult size and one pediatric size.

In further yet embodiments, one or more conduits of the elongated vent member may have a non-round profile, at least along the extraoral portion of the conduit. Both the internal shape and the external cross-sectional shape may be non-round, or just the external shape may be non-round. Exemplary non-round shapes useful for the purposes of the invention may include an oval shape, an elongated shape, an eye-shaped shape, etc.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, Aft BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A vented dental appliance for relief of bruxism comprising:
   an elongated vent member comprising a first fluid conduit between one or more intraoral vent openings positioned on an end of and along an intraoral portion thereof and an extraoral opening of an extraoral portion thereof, and
   an intraoral retainer configured for slidably retaining the elongated vent member positioned across thereof through a first aperture to provide fluid communication between an intraoral space and an extraoral space, thereby relieving intraoral suction,
   wherein the intraoral retainer further comprising a second aperture configured for retaining the elongated vent member, the second aperture is located adjacent to the first aperture, thereby using either the first aperture or the second aperture for retention of the elongated vent member facilitating position adjustment of the elongated vent member across the intraoral retainer, and
   wherein the elongated vent member is prevented from sliding across the intraoral retainer unless subjected to a pull force at or above a predetermined pull threshold.

2. The dental appliance as in claim 1, wherein the predetermined pull threshold is at least 0.25 lbs.

3. The dental appliance as in claim 1, wherein the predetermined pull threshold is at least 0.5 lbs.

4. The dental appliance as in claim 1, wherein the predetermined pull threshold is at least 0.75 lbs.

5. The dental appliance as in claim 1, wherein the elongated vent member comprises a second fluid conduit positioned across the intraoral retainer and configured to provide further fluid communication between the intraoral space and the extraoral space.

6. The dental appliance as in claim 5, wherein the first fluid conduit of the elongated vent member is positioned on a first side of the intraoral retainer, while the second fluid conduit of the elongated vent member is positioned on a second side thereof.

7. The dental appliance as in claim 1, wherein the intraoral retainer comprises a plurality of further apertures, each configured for individually retaining the elongated vent member, thereby providing a plurality of alternate positions of the elongated vent member across the intraoral retainer.

8. A vented dental appliance for relief of bruxism comprising:
   an elongated vent member comprising a first fluid conduit between one or more intraoral vent openings positioned at an end of and along an intraoral portion thereof and an extraoral opening of an extraoral portion thereof, and
   an intraoral retainer configured for retaining the elongated vent member positioned across thereof through a first aperture to provide fluid communication between an intraoral space and an extraoral space, thereby relieving intraoral suction,
   wherein the intraoral retainer further comprising a second aperture configured for retaining the elongated vent member, the second aperture is located adjacent to the first aperture, thereby using either the first aperture or the second aperture for retention of the elongated vent member facilitating position adjustment of the elongated vent member across the intraoral retainer.

9. The vented dental appliance as in claim 8, wherein the intraoral retainer contains a plurality of apertures configured for allowing alternative positioning of the elongated vent member across thereof.

10. The vented dental appliance as in claim 9, wherein the plurality of apertures are arranged to facilitate adjustment of horizontal positioning and vertical positioning of the elongated vent member across thereof.

11. The vented dental appliance as in claim 10, wherein the plurality of apertures are arranged in at least two parallel rows of apertures.

12. The vented appliance as in claim 11, wherein each row of apertures contains at least 3 apertures therein.

13. A vented dental appliance for relief of bruxism comprising:
   an elongated vent member comprising a first fluid conduit between multiple intraoral vent openings positioned along an intraoral portion thereof and an extraoral opening of an extraoral portion thereof, and
   an intraoral retainer configured for removably retaining the elongated vent member positioned across thereof through a first aperture to provide fluid communication between an intraoral space and an extraoral space, thereby relieving intraoral suction,
   wherein the intraoral retainer further comprising a second aperture configured for retaining the elongated vent member, the second aperture is located adjacent to the first aperture, thereby using either the first aperture or the second aperture for retention of the elongated vent member facilitating position adjustment of the elongated vent member across the intraoral retainer.

14. The vented dental appliance as in claim 13, wherein the elongated vent member further comprises at least one grommet positioned over the first fluid conduit and configured to define the position thereof across the intraoral retainer.

15. The vented dental appliance as in claim 14, wherein the at least one grommet has at least one leading edge on at least one side thereof, thereby facilitating sliding of the first fluid conduit across the aperture of the intraoral retainer.

16. The vented dental appliance as in claim 14, wherein the at least one grommet has an elongated cross-section.

17. The vented dental appliance as in claim 14, wherein the at least one grommet is slidable along the first fluid conduit upon applying a force exceeding a predetermined pull threshold.

18. The vented dental appliance as in claim 14, wherein the at least one grommet is permanently attached to the first fluid conduit and is located on the extraoral portion thereof.

\* \* \* \* \*